(12) United States Patent
Jeong

(10) Patent No.: US 8,475,730 B2
(45) Date of Patent: Jul. 2, 2013

(54) APPARATUS FOR SINGLE CELL SEPARATION AND POSITION FIXING

(75) Inventor: Ok Chan Jeong, Gimhae-si (KR)

(73) Assignee: Inje University Industry-Academic Cooperation Foundation, Gimhae-Si, Gyeongsangnam-Do (KR)

( * ) Notice: Subject to any disclaimer, the term of this patent is extended or adjusted under 35 U.S.C. 154(b) by 0 days.

(21) Appl. No.: 13/299,766

(22) Filed: Nov. 18, 2011

(65) Prior Publication Data

US 2013/0129578 A1     May 23, 2013

Related U.S. Application Data

(63) Continuation of application No. PCT/KR2011/008788, filed on Nov. 17, 2011.

(51) Int. Cl.
    *B01D 11/04*     (2006.01)
    *G01N 33/00*     (2006.01)

(52) U.S. Cl.
    USPC .......................................... 422/255; 422/417

(58) Field of Classification Search
    USPC .................................................. 422/255, 417
    See application file for complete search history.

(56) References Cited

U.S. PATENT DOCUMENTS

2004/0037739 A1*   2/2004   McNeely et al. ............... 422/58
2007/0243523 A1*   10/2007   Ionescu-Zanetti et al. ....... 435/4

* cited by examiner

*Primary Examiner* — Kevin Joyner
(74) *Attorney, Agent, or Firm* — Lucas & Mercanti, LLP

(57) ABSTRACT

The present invention relates to an apparatus for single cell trap and position fixing of the trapped cell thereof, and specifically, it induces cell movement from where fluid flows strongly to where the fluid flows weakly, by injecting pressed air to an air channel to modify a thin film of a vibrator, and therefore to induce the fluid flow. Further, the present invention relates to an apparatus which can fix the cell position as well as minimizing the external stimulation to the cells, wherein single cells are trapped in a region wherein the fluid flows are minimized and their positions are fixed using the effect that the fluid flows induced by the vibrators are offset one another because the vibrators are formed symmetrically one another.

7 Claims, 6 Drawing Sheets

APPARATUS FOR SINGLE CELL SEPARATION AND POSITION FIXING

CROSS-REFERENCE TO RELATED APPLICATIONS

This application is a continuation of PCT/KR2011/008788, filed Nov. 17, 2011, the contents of which are incorporated herein by reference.

FIELD OF THE INVENTION

The present invention relates to an apparatus for single cell trap and position fixing of the trapped cell thereof, and specifically, it induces cell movement from where fluid flows strongly to where the fluid flows weakly, by injecting pressed air to an air channel to modify a thin film of a vibrator, and therefore to induce the fluid flow.

Further, the present invention relates to an apparatus which can fix the cell position as well as minimizing the external stimulation to the cells, wherein single cells are trapped in a region where the fluid flows are minimized and their positions are fixed using the effect that the fluid flows induced by the vibrators are offset one another by interference in the middle of the plural vibrators because the plural vibrators are formed symmetrically one another.

BACKGROUND OF THE INVENTION

Nano-biotechnology (NBT) as the next generation fusion technology is a technology which can bring innovative advance to diagnosis and treatment of human disease, and its importance is growing.

Particularly, a biochip as one of representative areas of biotechnology is a biological information sensing device wherein biological materials such as DNA, protein, antibody, cell and the like are integrated in large scale on a solid substrate such as glass, silicone, polymer and the like, and it is a suitable technology to analyze trace amount of a sample very rapidly.

According to the development of cell technology, methodology which can effectively analyze only unit cell was demanded as cell study is further subdivided, and microengineering accelerated the study of the biochip by providing the methodology.

The biochip can be largely classified to a microarray chip and a microfluidic chip. The microarray chip is a chip wherein tens of millions or tens thousands of DNA, protein, carbohydrate, peptide and the like are arranged at certain interval, and a material subjected to analysis is treated thereto to analyze their binding pattern, and the microfluidic chip (or lab on a chip) is a chip to analyze pattern of reaction of the subjecting material to analysis with various biological molecules integrated on the chip or sensor while flowing out the subjecting material.

In the microfluidic chip, as a cell separation technique using a dielectrophoresis to separate single cell, there is a method using a negative/positive dielectrophoresis or a traveling wave dielectrophoresis alone, or using a dielectrophoresis migration or a dielectrophoresis retention, which combines the dielectrophoresis and the microfluidics. The dielectrophoresis migration or the dielectrophoresis retention has disadvantages that dielectric properties between cells should be largely different, and stress is added to the cells during separation.

Some ways were suggested to solve the problems, but a way to exclude external stress occurred in the process of single cell trap has not yet been suggested so far. The way to trap single cells without external stress is still remained as a problem to be solved not only for detailed single cell study, but also for the development of biotechnology.

SUMMARY OF THE INVENTION

Accordingly, it is an object of the present invention to provide an apparatus which can separate single cell without external stress and fix the position of the separated single cell.

In order to achieve the object, an apparatus for single cell separation and position fixing in accordance with one embodiment of the present invention is characterized by comprising:

a) the first layer containing a fluidic channel wherein fluid containing cells flows;

b) the second layer containing plural air channels wherein air is injected from the outside;

c) a glass substrate wherein the first and the second layers are laminated; and d) vibrators formed at the one ends of the air channels.

An apparatus for single cell separation and position fixing in accordance with one embodiment of the present invention is characterized that the first layer containing the fluidic channel and the second layer containing air channels are made of PDMS.

An apparatus for single cell separation and position fixing in accordance with one embodiment of the present invention is characterized that the vibrators formed thinner than the surrounding air channels.

An apparatus for single cell separation and position fixing in accordance with one embodiment of the present invention is characterized that the vibrators are located within the fluidic channel region of the first layer.

An apparatus for single cell separation and position fixing in accordance with one embodiment of the present invention is characterized that the vibrators vibrate by being modified according to patterns such as the pressure of air injected through the air channels of the second layer and air injection frequency, and the vibration of the vibrators is transmitted to the fluidic channel of the first layer.

An apparatus for single cell separation and position fixing in accordance with one embodiment of the present invention is characterized that each vibrator is connected to one of the air channel separately so as to control the vibration of the each vibrator by the pressure of the air injected through the air channel.

An apparatus for single cell separation and position fixing in accordance with one embodiment of the present invention is characterized that the plural vibrators are formed to a shape wherein the vibrators become four vortexes of a square.

An apparatus for single cell separation and position fixing in accordance with one embodiment of the present invention is characterized that the center of the plural vibrators which form four vertexes of the square become a cell separation and position fixing region.

An apparatus for single cell separation and position fixing in accordance with one embodiment of the present invention is characterized by comprising plural cell separation and position fixing regions.

ADVANTAGEOUS EFFECTS OF THE INVENTION

The apparatus according to the present invention for single cell separation and position fixing forms parts of a channel wherein cell fluid flows to vibrators, and uses a way to induce the movement of the cells contained in the fluid from where fluid flows strongly to where the fluid flows weakly by modifying the vibrators by air, which is injected into air channels connected to the vibrators, followed by transmitting the vibration of the vibrators to the fluid containing the cells to induce the fluid flow. Therefore, the apparatus can separate single cells and fix their position without any external stimulation

BRIEF DESCRIPTION OF DRAWINGS

The above and other objects and features of the present invention will become apparent from the following description of the invention taken in conjunction with the following accompanying drawings, which respectively show.

DETAILED DESCRIPTION OF THE INVENTION

Hereinafter, the present invention is described in detail according to the following examples without limiting its scope.

Figure 1:
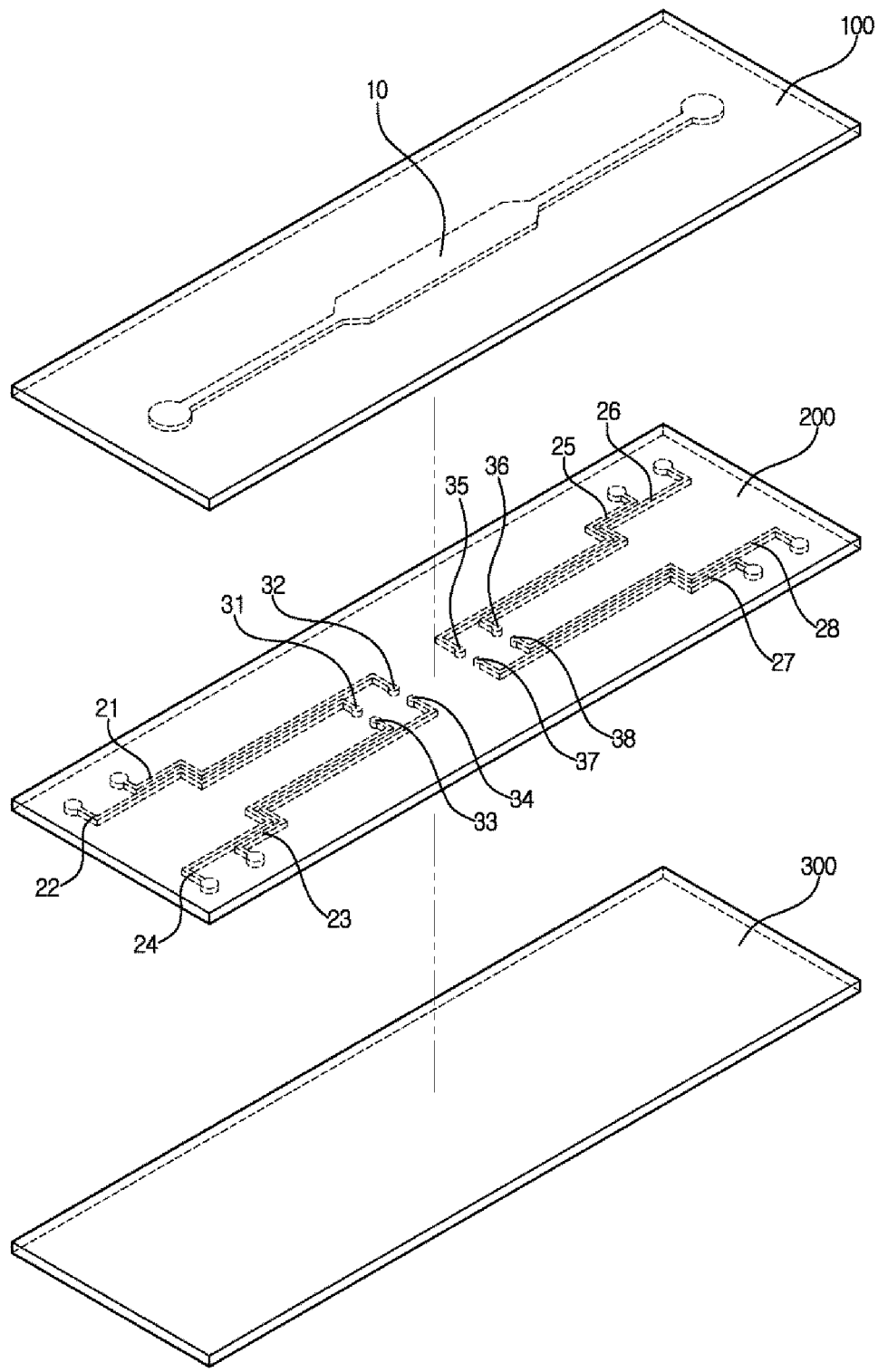
FIG. 1: An oblique view of the apparatus for single cell separation and position fixing according to the present invention wherein the first layer, the second layer and a substrate are separated.

An exploded oblique view of the apparatus for single cell separation and position fixing according to the present invention is represented in FIG. 1. As shown in FIG. 1, the apparatus for single cell separation and position fixing according to the present invention consists of the first layer (100) containing the fluidic channel (10) wherein fluid containing cells flows; the second layer (200) containing plural air channels (21, 22, 23, 24, 25, 26, 27 and 28) wherein air is injected from the outside; a substrate (300); and plural vibrators (31, 32, 33, 34, 35, 36, 37 and 38) formed at the internal ends of the air channels.

It is preferred that the fluidic channel has a region of cell separation and position fixing in the middle of the fluidic channel, and the vibrators are located in the region of the fluidic channel to move the cells flowing in the fluidic channel. Further, it is more preferred that the vibrators are included in the region of cell separation and position fixing (P region marked with dotted line in FIG. 2) which is formed in the middle of the fluidic channel because it is convenient to observe the cell movement in the fluidic channel using a microscope.

In the apparatus for single cell separation and position fixing according to one embodiment of the present invention, the fluidic channel of the first layer and the air channels of the second layer are characterized by being made of PDMS.

Because the fluidic channel and the air channels are prepared with a transparent PDMS material by soft lithography method, the observation using a microscope is easy and the production cost and time can be reduced.

The substrate (300) may be any one which can fix or support the laminated first and second layers made of PDMS but not limited thereto, and is not limited, and it is made of glass, acryl or other transparent material, preferably.

Figure 2:
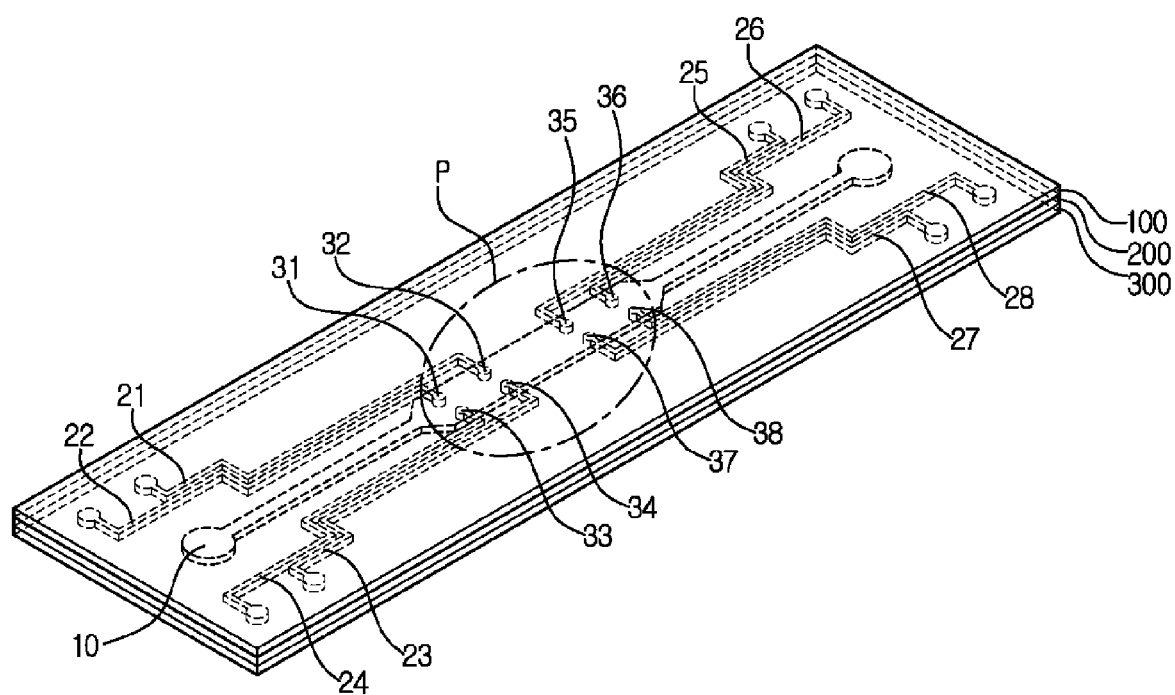
FIG. 2: A view representing the apparatus for single cell separation and position fixing according to the present invention which is formed by laminating the first layer, the second layer and a substrate.
Figure 3:
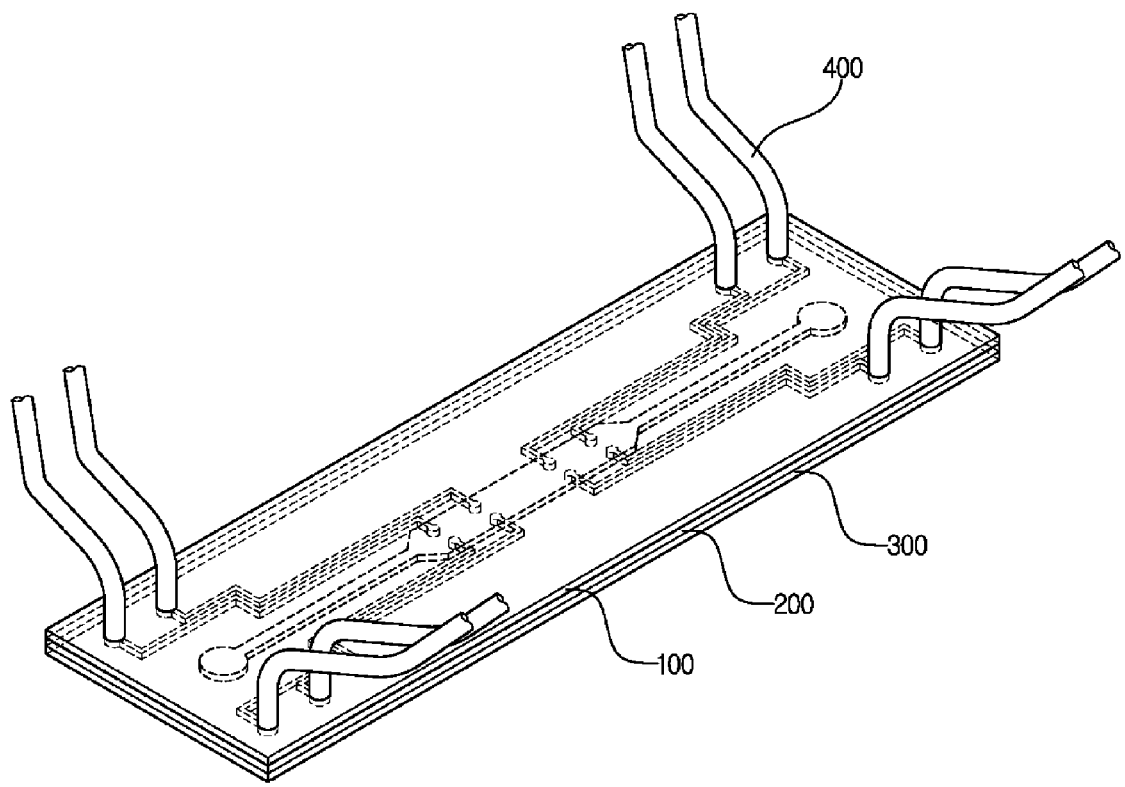
FIG. 3: A view representing the form of the apparatus for single cell separation and position fixing according to the present invention wherein injection tubes are installed to the air channels in the second layer.

The first layer containing the fluidic channel and the second layer containing the air channels are laminated to the substrate and adjoined. When the first and the second layers are laminated to the substrate, the channel-formed sides are laminated while facing down and adjoined, and inlets of the air channels and an inlet of the fluidic channel are formed using a punch. The form wherein the first layer, second layer and the substrate are laminated is shown in FIG. 2, and the form wherein external air injection tubes (400) are inserted into the inlets of the air channels after forming the inlets of the air channels and the inlet of the fluidic channel using a punch is shown in FIG. 3.

Figure 4:
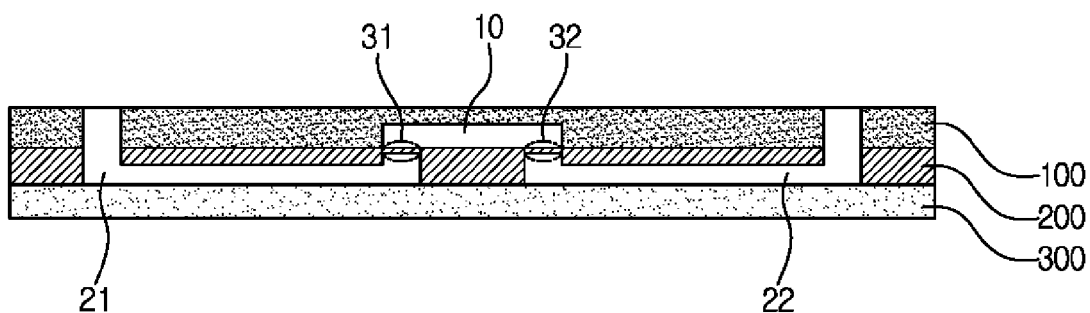
FIG. 4: A cross-sectional diagram of the apparatus for single cell separation and position fixing according to the present invention of FIG. 1.

A cross-sectional diagram of the apparatus for single cell separation and position fixing according to the present invention of FIG. 1 is represented in FIG. 4. As shown in FIG. 4, the apparatus for single cell separation and position fixing according to one embodiment of the present invention is prepared by adjoining the second layer (200) containing the air channels (21 and 22), the first layer (100) containing the fluidic channel (10), and a substrate (300).

The vibrators (31 and 32) are formed at the one ends of the air channels of the second layer and made thinner than the surrounding parts. In the apparatus for single cell separation and position fixing according to the one embodiment of the present invention, the vibrators are characterized that thin films of the vibrators are modified according to patterns such as the pressure of air injected through the air channels of the second layer and air injection frequency, the pressure of the modified vibrators is transmitted to the fluidic channel of the first layer, and therefore, the fluid flow is induced. In the present invention, the vibrators (31 and 32) are prepared relatively thinner that the surrounding parts to minimize the modification of the channel due to application of the pressed air and to make only the vibrators sensitively react.

Figure 5:
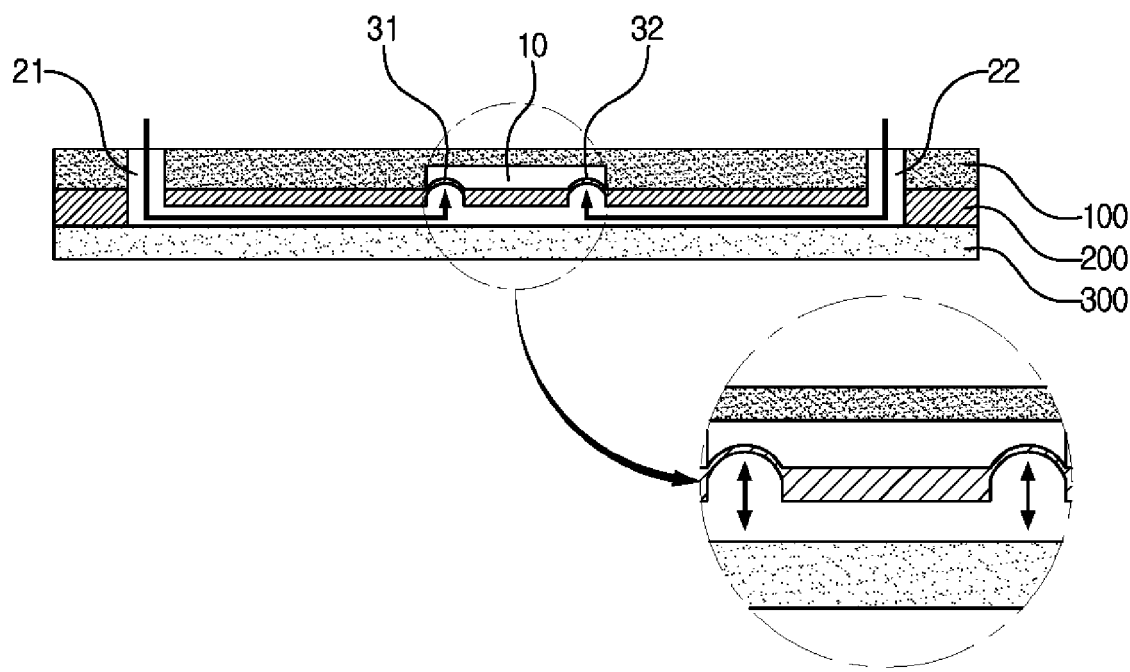
FIG. 5: A diagram showing a process of transmitting vibration to the fluidic channel caused by vibrating the vibrator by air injected into the air channels in the apparatus for single cell separation and position fixing according to the present invention.

Mechanism of the apparatus of the present invention for single cell separation and position fixing is represented in FIG. 5. As shown in FIG. 5, when air is injected from the outside into the air channels (21 and 22) of the apparatus for single cell separation and position fixing of the present invention, the vibrators (31 and 32), which are made thinner than the surrounding parts are modified by being swollen up, and the modifications of the vibrators are delivered to the fluid in the fluidic channel (10) to induce the fluid flow. Due to this, the cells move from where fluid flows strongly to where the fluid flows weakly.

The apparatus for single cell separation and position fixing according to one embodiment of the present invention is characterized that vibration of each vibrator can be separately controlled by the pressure of air injected through the air channels because one of the vibrators is connected to only one of the air channels, and each vibrator is independent from the rest of the vibrators. Namely, in the present invention, the cells can be moved to the desired position because vibration of one of the vibrators can be separately controlled by controlling the amount of air injected to one air channel and frequency.

In the apparatus for single cell separation and position fixing according to one embodiment of the present invention, it is characterized that the plural vibrators are formed to keep equal interval one another, preferably, and specifically, the vibrators form a square. Namely, in the present invention, the fluid flows induced from the plural vibrators forming a square are offset in the middle of the plural vibrators according to wave interference principle, and the position of the cells moved to the middle of the plural vibrators can be maintained.

Figure 6:
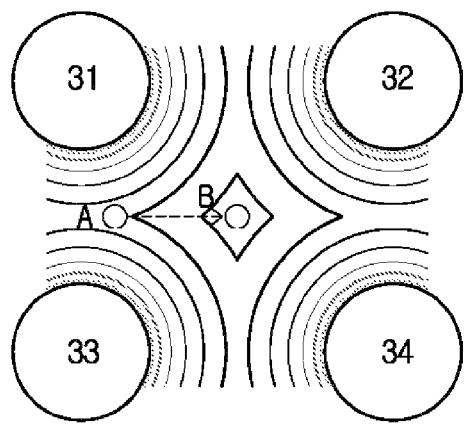
FIG. 6: A diagram showing a process of moving cells and fixing their positions between the plural vibrators.
Figure 6:
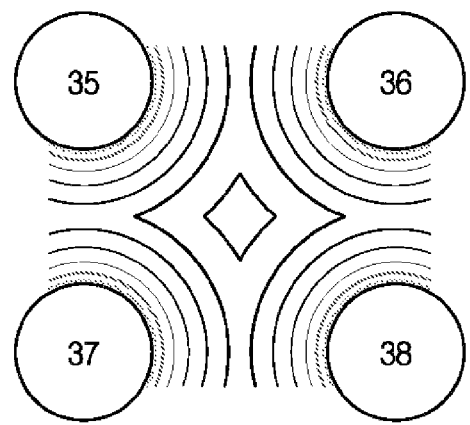

A form of the plural vibrators of the apparatus for single cell separation and position fixing of the present invention and a process of cell separation and position fixing are represented in FIG. 6.

As shown in FIG. 6, in the present invention, the plural vibrators (31 to 38) are formed that four vibrators (31, 32, 33 and 34) become vertexes of the square. At the point near each vibrator, movement is formed by strong vibration, and at the point far from the vibrator, movement is formed by weak vibration. Therefore, the fluid flow is induced from the point which is near the vibrator and has strong vibration to the point which is far from the vibrator and has weak vibration, and it causes the cell movement in the fluid.

Further, in the present invention, each vibrator (31 to 38) is connected to one of the air channels, respectively, so as to control vibration of each vibrator.

Namely, in order to move the cell of position A to position B in FIG. 6, the vibration of the vibrators (31 and 33) is controlled to be large by firstly increasing the pressure of air injected into the vibrators (31 and 33) near the cell and frequency. Then, after moving the cells to the center of the plural vibrators, vibration of the four vibrators (31, 32, 33 and 34) is equally maintained to offset the fluid flows one another in the middle of the plural vibrators, and therefore, the cell position can be kept. Namely, the apparatus of the present invention for single cell separation and position fixing induces the cell movement by controlling physical force added to the fluid containing cells, and consequently, each single cell can be separated and its position can be fixed without any external stress.

In the apparatus of the present invention for single cell separation and position fixing, it is possible to comprise plural cell separation and position fixing regions formed by the four vibrators making a square.

As shown in FIG. 1, there can be plural cell separation and position fixing regions, i.e., the one region formed with the vibrators of 31 to 34 and the other region formed with the vibrators of 35 to 38. In the case of forming plural cell separation and position fixing regions, it is possible to separate plural cells according to the fluid flow in the fluidic channel, and to fix their positions.

While the invention has been described with respect to the above specific embodiments, it should be recognized that various modifications and changes may be made and also fall within the scope of the invention as defined by the claims that follow.

What is claimed is:

1. An apparatus for single cell separation and position fixing, which comprises:
   a) a first layer containing a fluidic channel wherein fluid containing cells flows;
   b) a second layer containing plural air channels wherein air is injected from the outside;
   c) a glass substrate wherein the first and the second layers are laminated; and
   d) thin film vibrators which are located between the air and fluidic channels and formed at one end of each of the air channels,
   wherein the plural thin film vibrators form a square and the plural thin film vibrators are located at each corner of a square area.

2. The apparatus for single cell separation and position fixing of claim 1, wherein the first layer containing the fluidic channel and the second layer containing air channels are made of PDMS.

3. The apparatus for single cell separation and position fixing of claim 1, wherein the thin film vibrators are thinner than the surrounding air channels.

4. The apparatus for single cell separation and position fixing of claim 1, wherein the thin film vibrators vibrate by the pressure of air injected through the air channels of the second layer, and the pressure of the thin film vibrators is transmitted to the fluidic channel of the first layer.

5. The apparatus for single cell separation and position fixing of claim 1, wherein one of the thin film vibrators is connected to one of the air channel so as to separately control the vibration of the vibrator by the pressure of the air injected through the air channel.

6. The apparatus for single cell separation and position fixing of claim 1, wherein the center of the square formed by the plural thin film vibrators becomes a cell separation and position fixing region.

7. The apparatus for single cell separation and position fixing of claim 1, which comprises plural cell separation and position fixing regions formed by the plural thin film vibrators.

* * * * *